(12) United States Patent
Rowlandson et al.

(10) Patent No.: US 7,415,304 B2
(45) Date of Patent: Aug. 19, 2008

(54) SYSTEM AND METHOD FOR CORRELATING IMPLANT AND NON-IMPLANT DATA

(75) Inventors: G. Ian Rowlandson, Milwaukee, WI (US); David E. Albert, Oklahoma City, OK (US)

(73) Assignee: GE Medical Systems Information Technologies, Inc., Waukesha, WI (US)

( * ) Notice: Subject to any disclaimer, the term of this patent is extended or adjusted under 35 U.S.C. 154(b) by 408 days.

(21) Appl. No.: 10/824,964

(22) Filed: Apr. 15, 2004

(65) Prior Publication Data

US 2005/0234356 A1   Oct. 20, 2005

(51) Int. Cl.
A61B 5/04   (2006.01)
(52) U.S. Cl. ..................................... 600/513
(58) Field of Classification Search .............. 600/510, 600/513, 515; 607/60, 59, 32, 513, 9, 27, 607/30; 128/903
See application file for complete search history.

(56) References Cited

U.S. PATENT DOCUMENTS

| | | | |
|---|---|---|---|
| 3,554,187 A | 1/1971 | Glassner et al. |
| 3,658,055 A | 4/1972 | Abe et al. |
| 3,759,248 A | 9/1973 | Valiquette |
| 3,821,948 A | 7/1974 | King |
| 3,902,479 A | 9/1975 | Chaumet |
| 3,952,731 A | 4/1976 | Worstencroft |
| 4,124,894 A | 11/1978 | Vick et al. |
| 4,136,690 A | 1/1979 | Anderson et al. |
| 4,170,992 A | 10/1979 | Dillman |
| 4,181,135 A | 1/1980 | Andresen et al. |
| 4,202,340 A | 5/1980 | Langer et al. |
| 4,316,249 A | 2/1982 | Gallant et al. |
| 4,417,306 A | 11/1983 | Citron et al. |
| 4,422,459 A | 12/1983 | Simson |
| 4,432,375 A | 2/1984 | Angel et al. |
| 4,457,315 A | 7/1984 | Bennish |
| 4,458,691 A | 7/1984 | Netravali |
| 4,458,692 A | 7/1984 | Simson |
| 4,475,558 A | 10/1984 | Brock |
| 4,492,235 A | 1/1985 | Sitrick |

(Continued)

FOREIGN PATENT DOCUMENTS

DE   2604460   8/1977

(Continued)

OTHER PUBLICATIONS

Speranza et al., 'Beat-to-beat measurement and analysis of the R-T interval in 24 h ECG Holter recordings,' Med and Biol Eng & Comput, 1993, 31, pp. 487-494.

(Continued)

*Primary Examiner*—Carl H. Layno
*Assistant Examiner*—Jon-Eric C. Morales
(74) *Attorney, Agent, or Firm*—Andrus, Sceales, Starke & Sawall, LLP

(57) ABSTRACT

A system and method for analyzing cardiac data acquired from a patient having an implant. The system can acquire non-implant cardiac data and implant cardiac data from the patient. The system can synchronize the non-implant cardiac data and the implant cardiac data and can correlate the non-implant cardiac data with the implant cardiac data to determine a cardiac condition of the patient.

5 Claims, 3 Drawing Sheets

U.S. PATENT DOCUMENTS

| | | | |
|---|---|---|---|
| 4,499,904 A | 2/1985 | Sidorenko et al. | |
| 4,519,395 A | 5/1985 | Hrushesky | |
| 4,583,553 A | 4/1986 | Shah et al. | |
| 4,589,420 A | 5/1986 | Adams et al. | |
| 4,603,703 A | 8/1986 | McGill et al. | |
| 4,616,333 A * | 10/1986 | Shimoni | 708/813 |
| 4,616,659 A | 10/1986 | Prezas et al. | |
| 4,665,485 A | 5/1987 | Lundy et al. | |
| 4,679,144 A | 7/1987 | Cox et al. | |
| 4,680,708 A | 7/1987 | Ambos et al. | |
| 4,732,157 A | 3/1988 | Kaplan et al. | |
| 4,796,638 A | 1/1989 | Sasaki | |
| 4,802,491 A | 2/1989 | Cohen et al. | |
| 4,832,038 A | 5/1989 | Arai et al. | |
| 4,854,327 A | 8/1989 | Kunig | |
| 4,860,762 A | 8/1989 | Heumann et al. | |
| 4,896,677 A | 1/1990 | Kaneko et al. | |
| 4,924,875 A | 5/1990 | Chamoun | |
| 4,928,690 A | 5/1990 | Heilman et al. | |
| 4,938,228 A | 7/1990 | Righter et al. | |
| 4,951,680 A | 8/1990 | Kirk et al. | |
| 4,955,382 A | 9/1990 | Franz et al. | |
| 4,957,115 A | 9/1990 | Selker | |
| 4,958,641 A | 9/1990 | Digby et al. | |
| 4,972,834 A | 11/1990 | Begemann et al. | |
| 4,974,162 A | 11/1990 | Siegel et al. | |
| 4,974,598 A | 12/1990 | John | |
| 4,977,899 A | 12/1990 | Digby et al. | |
| 4,979,510 A | 12/1990 | Franz et al. | |
| 4,989,610 A | 2/1991 | Patton et al. | |
| 4,998,535 A | 3/1991 | Selker et al. | |
| 5,000,189 A | 3/1991 | Throne et al. | |
| 5,010,888 A | 4/1991 | Jadvar et al. | |
| 5,020,540 A | 6/1991 | Chamoun | |
| 5,025,795 A | 6/1991 | Kunig | |
| 5,042,497 A | 8/1991 | Shapland | |
| 5,092,341 A | 3/1992 | Kelen | |
| 5,109,862 A | 5/1992 | Kelen et al. | |
| 5,117,833 A | 6/1992 | Albert et al. | |
| 5,117,834 A | 6/1992 | Kroll et al. | |
| 5,148,812 A | 9/1992 | Verrier et al. | |
| 5,188,116 A | 2/1993 | Pommrehn et al. | |
| 5,201,321 A | 4/1993 | Fulton | |
| 5,234,404 A | 8/1993 | Tuttle et al. | |
| 5,253,650 A | 10/1993 | Wada | |
| 5,265,617 A | 11/1993 | Verrier et al. | |
| 5,276,612 A | 1/1994 | Selker | |
| 5,277,188 A | 1/1994 | Selker | |
| 5,277,190 A | 1/1994 | Moulton | |
| 5,323,783 A | 6/1994 | Henkin et al. | |
| 5,343,870 A | 9/1994 | Gallant et al. | |
| 5,423,878 A | 6/1995 | Franz | |
| 5,437,285 A | 8/1995 | Verrier et al. | |
| 5,501,229 A | 3/1996 | Selker et al. | |
| 5,560,370 A | 10/1996 | Verrier et al. | |
| 5,570,696 A | 11/1996 | Arnold et al. | |
| 5,718,233 A | 2/1998 | Selker et al. | |
| 5,724,983 A | 3/1998 | Selker et al. | |
| 5,747,274 A | 5/1998 | Jackowski | |
| 5,819,007 A | 10/1998 | Elghazzawi | |
| 5,819,741 A | 10/1998 | Karlsson et al. | |
| 5,921,940 A | 7/1999 | Verrier et al. | |
| 5,935,082 A | 8/1999 | Albrecht et al. | |
| 5,948,005 A * | 9/1999 | Valikai et al. | 607/32 |
| 6,059,724 A | 5/2000 | Campell et al. | |
| 6,067,466 A | 5/2000 | Selker et al. | |
| 6,099,469 A | 8/2000 | Armstrong et al. | |
| 6,129,677 A * | 10/2000 | Sohma et al. | 600/513 |
| 6,142,078 A | 11/2000 | Lachajewski | |
| 6,169,919 B1 | 1/2001 | Nearing et al. | |
| 6,334,192 B1 | 12/2001 | Karpf | |
| 6,385,485 B1 * | 5/2002 | Ripart | 600/513 |
| 6,394,952 B1 | 5/2002 | Anderson et al. | |
| 6,443,889 B1 | 9/2002 | Groth et al. | |
| 6,450,954 B1 | 9/2002 | Selker | |
| 6,453,191 B2 | 9/2002 | Krishnamachari | |
| 6,458,086 B1 * | 10/2002 | Franco et al. | 600/526 |
| 6,507,753 B1 | 1/2003 | Xue et al. | |
| 6,640,134 B2 * | 10/2003 | Raymond et al. | 600/513 |
| 6,647,287 B1 * | 11/2003 | Peel et al. | 600/513 |
| 6,654,631 B1 * | 11/2003 | Sahai | 600/509 |
| 6,668,188 B2 * | 12/2003 | Sun et al. | 600/513 |
| 7,054,679 B2 * | 5/2006 | Hirsh | 600/523 |
| 7,074,194 B2 * | 7/2006 | Crosby et al. | 600/508 |
| 2002/0099302 A1 * | 7/2002 | Bardy | 600/510 |
| 2002/0123672 A1 * | 9/2002 | Christophersom et al. | 600/300 |
| 2003/0204145 A1 * | 10/2003 | Manolas | 600/513 |
| 2005/0103351 A1 * | 5/2005 | Stomberg et al. | 128/898 |

FOREIGN PATENT DOCUMENTS

| | | |
|---|---|---|
| DE | 3303104 | 8/1984 |
| DE | 4024360 | 3/1991 |
| EP | 0080821 | 6/1983 |
| FR | 2539978 | 8/1984 |
| GB | 2070871 | 9/1981 |
| WO | WO81/02832 | 10/1981 |

OTHER PUBLICATIONS

Narayanaswamy et al., 'Selective beat signal averaging and spectral analysis of beat intervals to determine the mechanisms of premature ventricular contractions,' University of Oklahoma Health Sciences Center, May 1993, pp. 81-84.

Laks et al., 'ECG computer program developed for a retrospective and prospective study of the Pardee T wave,' Department of Medicine, UCLA School of Medicine, Harbor-UCLA Medical Center, Torrence, CA, 1992, pp. 365-368.

Makarov et al., 'Holter monitoring in the long QT syndrome of children and adolescents,' Cor Vasa, 1990, 32(6), pp. 474-483.

Navarro-Lopez et al., 'Isolated T wave alternans elicited by hypocalcemia in dogs,' Electrocardiology, 1978, 11(2), pp. 103-108.

Little et al., 'Torsade de Pointes and T-U wave alternans associated with arsenic poisoning,' Pace, 1990, 13, pp. 164-170.

Weintraub et al., 'The congenital long QT syndromes in childhood,' Journal of the American College of Cardiology, Sep. 1990, 16(3), pp. 674-680.

Bibler et al., 'Recurrent ventricular tachycardia due to pentamidine-induced cardiotoxicity,' Chest, Dec. 1988, 94(6), pp. 1303-1306.

Ahnve et al., 'Circadian variations in cardiovascular parameters during sleep deprivation, A noninvasive study of young healthy men,' European Journal of Applied Physiology, 1981, 46, pp. 9-19.

Surawicz, 'ST-segment, T-wave, and U-wave changes during myocardial ischmeia and after myocardial infarction,' Canadian Journal of Cardiology, Supplement A, Jul. 1986, pp. 71A-84A.

Stroobandt et al., 'Simultaneous recording of atrial and ventricular monophasic action potentials: monophasic action potential duration during atrial pacing, ventricular pacing, and ventricular fibrillation,' Pace, Jul.-Aug. 1985, 8, pp. 502-511.

Sharma et al., 'Romano-Ward prolonged QT syndrome with intermittant T wave alternans and atrioventricular block,' American Heart Journal, 1981, pp. 500-501.

Navarro-Lopez et al., 'Isolated T wave alternans,' American Heart Journal, 1978, pp. 369-374.

Mitsutake et al., 'Usefulness of the Valsalva Maneuver in management of the long QT syndrome,' Circulation, 1981, 63(5), pp. 1029-1035.

Nearing et al., 'Personal computer system for tracking cardiac vulnerability by complex demodulation of the T wave,' American Physiological Society, 1993, pp. 2606-2612.

Joyal et al., 'ST-segment alternans during percutaneous transluminal coronary angioplasty,' Division of Cardiology, Department of Medicine, University of Florida and the Veterans Administration Medical Center, Jun. 1984, pp. 915-916.

Schwartz et al., 'Electrical alternation of the T-wave: clinical and experimental evidence of its relationship with the sympathetic nervous system and with the long Q-T syndrome,' American Heart Journal, Jan. 1975, 89(1), pp. 45-50.

Schwartz, 'Idiopathic long QT syndrome: progress and questions,' American Heart Journal, Feb. 1985, 109(2), pp. 399-411.

Verrier et al., 'Electrophysiologic basis for T wave alternans as an index of vulnerability to ventricular fibrillation,' Journal of Cardiovascular Electrophysiology, May 1994, 5(5), pp. 445-461.

Verrier et al., 'Behavioral states and sudden cardiac death,' Pace, Sep. 1992, 15, pp. 1387-1393.

Turitto et al., 'Alternans of the ST segment in variant angina,' Chest, Mar. 1988, 93(3), pp. 587-591.

Ring et al., 'Exercise-induced ST segment alternans,' American Heart Journal, May 1986, 111(5), pp. 1009-1011.

Wayne et al., 'Exercise-induced ST segment alternans,' Chest, May 1983, 83(5), pp. 824-825.

Verrier et al., 'Ambulatory electrocardiogram-based tracking of T wave alternans in postmyocardial infarction patients to assess risk of cardiac arrest or arrhythmic death,' Journal of Cardiovascular Electrophysiology, Jul. 2003, 14(7), pp. 705-711.

Ryan, et al.; ACC/AHA Guidelines for the Management of Patients With Acute Myocardial Infarction; Journal of the American College of Cardiology; vol. 28, No. 5, Nov. 1, 1996; 1328-428.

Ryan, et al.; 1999 Update: ACC/AHA Guidelines for the Management of Patients With Acute Myocardial Infarction; Journal of the American College of Cardiology; vol. 34, No. 3, Sep. 1999; 890-911.

Circulation; American Heart Association; ECC Guidelines, Part 7: The Era of Reperfusion; http://circ.ahajournals.org/cgi/content/full/102/suppl_1/I-172?maxtoshow+HIRA=10&hits=10&RES; 2000; 102: I-172.

Kudenchuk, et al., Accuracy of Computer-Interpreted Electrocardiography in Selecting Patients for Thrombolytic Therapy; Journal of the American College of Cardiology; vol. 17, No. 7, Jun. 1991, 1486-91.

O'Rourke, et al.; Accuracy of a Portable Interpretive ECG Machine in Diagnosis of Acute Evolving Myocardial Infarction; Aust NZ J Med 1992; 22; 9-13.

Braunwald, et al.; ACC/AHA Guidelines for the Management of Patients With Unstable Angina and Non-ST-Segment Elevation Myocardial Infarction, Journal of the American College of Cardiology; vol. 36, No. 3, Sep. 2000; 970-1062.

* cited by examiner

SYSTEM AND METHOD FOR CORRELATING IMPLANT AND NON-IMPLANT DATA

BACKGROUND OF THE INVENTION

A pacemaker's main purpose is to analyze the function of the heart's electrical system and to keep the electrical system operating properly. A pacemaker can prevent the cardiac problems associated with slow heart rhythms (e.g., congestive heart failure, fainting, death, etc.). Pacemakers are necessary because, while there are many medications that prevent the heart from operating too quickly, there are only a few medications that can make the heart operate more quickly. Pacemakers have become a reliable means of helping people live longer and improve their lifestyles despite having a slow heart rhythm.

An automatic internal cardioverter defibrillator ("AICD") is an electronic device that is implanted in a pocket formed in the chest wall that senses the heart's rhythm and can deliver a powerful shock to the heart. The AICD automatically detects certain arrhythmias (e.g., ventricular fibrillation, ventricular tachycardia, atrial fibrillation, etc.) and delivers a shock to the heart to terminate the arrhythmia.

Both pacemakers and AICDs provide artificial stimulation for the management of rhythm and/or improved heart function. Both pacemakers and AICDs include electronic circuitry that stores information about the heart as it monitors the heart rhythm and delivers therapy. Caregivers can review this stored information by using a programmer or interrogator that communicates with the pacemaker or AICD through the skin. Caregivers are able to review the heart's rhythms, arrhythmia episodes, and device operation over a period of time with the programmer or interrogator.

Conventionally, caregivers review the implant data gathered by the programmer or interrogator independently of other cardiac data available for the patient.

BRIEF DESCRIPTION OF THE INVENTION

In one embodiment, the invention includes a method of analyzing cardiac data acquired from a patient having an implant. The method comprises acquiring non-implant cardiac data and implant cardiac data from the patient, synchronizing the non-implant cardiac data and the implant cardiac data, and correlating the non-implant cardiac data with the implant cardiac data to determine a cardiac condition of the patient.

DETAILED DESCRIPTION

Figure 1:
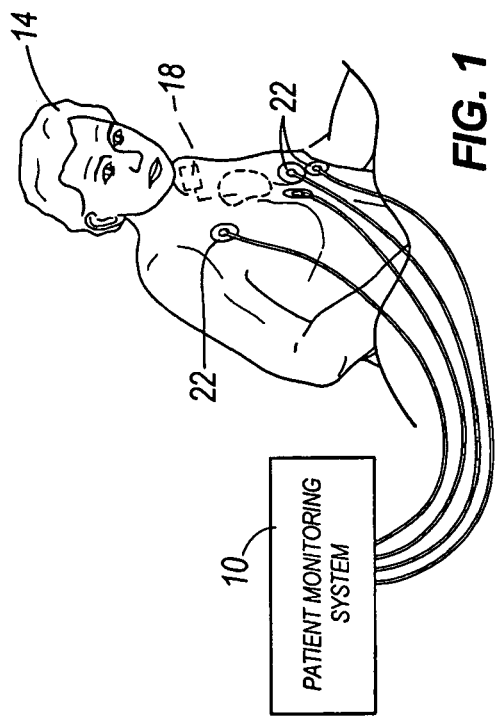
FIG. 1 illustrates a patient having an implant and being connected to a patient monitoring system.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect.

In addition, it should be understood that embodiments of the invention include both hardware and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

Generally, pacemakers and AICDs can be programmed in any suitable manner to accommodate the needs of the patient. The pacemaker can be programmed wirelessly using a handheld programmer that communicates with the pulse generator through the patient's skin using radio frequencies. For example, the following parameters can be programmed: the strength and duration of the impulse delivered to the heart muscle, the speed of the pacemaker, and the time period between stimulating the atrium and the ventricle.

Periodically, the pulse generator can be interrogated in order to download patient information and cardiac data (e.g., electrocardiograms; "ECGs") and in order to monitor the operation of the pacemaker. The pulse generator can also be reprogrammed to extend the battery life and/or to adjust the operational parameters to accommodate changes in the patient's lifestyle.

Most electronic cardiac implants (e.g., pacemakers and AICDs) acquire diagnostic and therapeutic information and patient data. It should be noted that the invention is not limited to pacemakers and AICDs. Rather, any electronic cardiac implant can be utilized with the embodiments of the invention. Caregivers for patients with electronic cardiac implants can use information from a variety of sources to monitor and treat the patient, including data acquired from the implant, as well as from other sources. However, as the implant patient moves throughout the medical care system, all caregivers may not have access to the implant data to assist in making diagnostic and treatment decisions. In contrast, other cardiac monitoring that acquires non-implant data (e.g., bedside monitoring and resting 12-lead ECGs) is used routinely in the medical care system, and the results are generally readily available to most caregivers.

These other cardiac monitoring techniques can record significant patient clinical events that are reflected in the non-implant data. In some embodiments of the invention, the non-implant data can be correlated with the data acquired by the electronic implant. The correlation of the non-implant data and the implant data can increase the usefulness of the patient's overall data and can provide a bigger clinical picture from which to make medical diagnoses and treatment recommendations for the patient.

FIG. 1 illustrates a patient monitoring system 10 according to one embodiment of the invention that can be connected to a patient 14 having an implant 18. The patient monitoring system 10 can include, but is not limited to, one or more medical devices, such as bedside monitors, ECG machines, Holter monitors, etc. The patient 14 can be connected to the patient monitoring system 10 via external electrodes 22 that can be connected to the patient's chest in any suitable standard or non-standard ECG configuration. The electrodes 22 can acquire one or more leads of the patient's ECG. Generally, at least two electrodes 22 must be positioned on the patient's chest to acquire one lead of ECG data. If the patient 14 is experiencing chest pain or other heart-related symptoms, caregivers can prescribe various tests using the data acquired by the electrodes 22 to diagnose the patient's cardiac problems. For example, the patient 14 can undergo a standard or non-standard ECG test, a stress test, a stress-echo test, a stress-nuclear test, and/or other medical test procedures to diagnose any cardiac problems. The patient 14 can also undergo other cardiac tests that do not use the external electrodes 22 to acquire data, such as cardiac catheterization procedures and electrophysiology studies.

Figure 2:
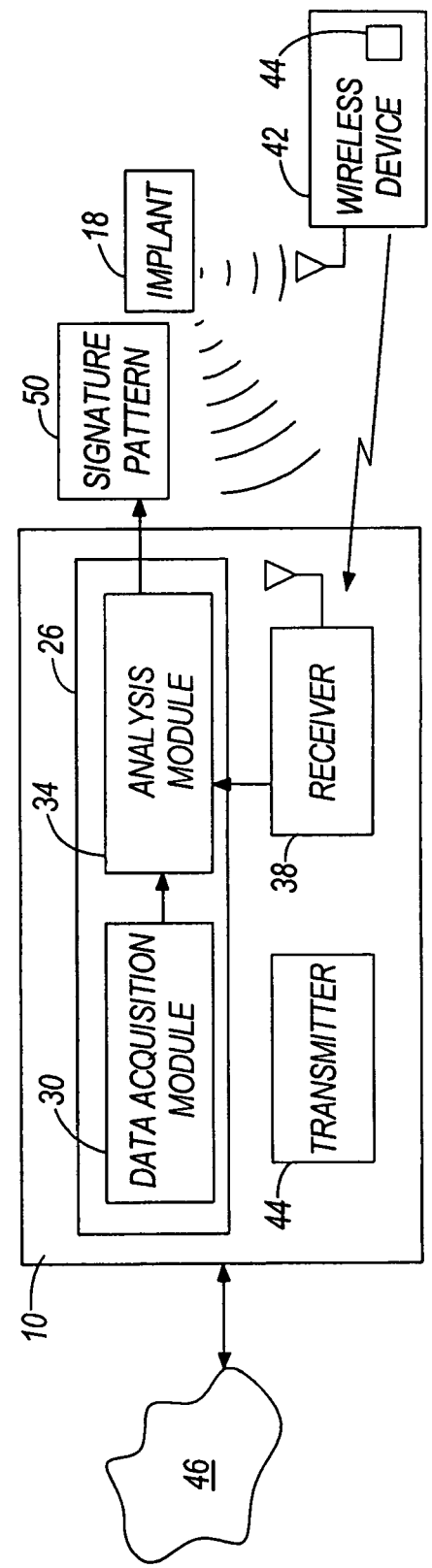
FIG. 2 is a schematic diagram of a system for correlating implant and non-implant data according to one embodiment of the invention.

As shown schematically in FIG. 2, the patient monitoring system 10 can include a software program 26. The software program 26 can include a data acquisition module 30 and an analysis module 34. The data acquisition module 30 can acquire clinical data from the patient 14 and can transmit the clinical data to the analysis module 34. The analysis module 34 can analyze the clinical data received from the data acquisition module 30. In some embodiments, as shown in FIG. 2, the data acquisition module 30 can be included in the patient monitoring system 10. In other embodiments, the data acquisition module 30 can be independent of the patient monitoring system 10 and can be connected to the patient monitoring system 10 via a hardwired or wireless connection.

The patient monitoring system 10 can also include hardware, such as a processor, I/O interfaces, and storage devices or memory. In addition, the patient monitoring system 10 can include input devices (such as a keyboard and a mouse) and output devices (such as a monitor). The patient monitoring system 10 can further include peripherals (such as a printer and a scanner). The patient monitoring system 10 can still further include other software, such as a display application.

As shown in FIG. 2, the patient monitoring system 10 can include a receiver 38 for receiving clinical data from a wireless device 42 or directly from the implant 18. The patient monitoring system 10, the wireless device 42, and/or the electrical implant 18 can include any suitable software and/or hardware (not shown) to communicate wirelessly with one another.

One or both of the patient monitoring system 10 and the wireless device 42 can include a transmitter 44 that can periodically transmit a polling signal in order to determine if any patient in the vicinity has an implant 18. The polling signal can cause the implant 18 to begin transmitting data that can be received by the receiver 38 and/or wireless device 42. In some embodiments, if the receiver 38 or wireless device 42 receives a signal from the implant 18, the software program 26 can automatically detect that the patient 14 has an implant 18 and can initiate the data acquisition module 30 of the patient monitoring system or the wireless device 42 to begin acquiring data from the implant 18. As a result, when a patient 14 enters a room with the patient monitoring system 10, the patient monitoring system 10 can automatically detect that the patient 14 has an implant 18 and can begin acquiring clinical data from the implant 18.

The patient monitoring system 10 can include a plurality of systems, modules, and/or components that can communicate over a network 46 (as shown schematically in FIG. 2). The patient monitoring system 10 can communicate with other devices (not shown), such as other medical devices, computer terminals, servers, and databases, via the network 46. The network 46 can be built according to any networking technology or topology or combinations of technologies and topologies and may include multiple sub-networks. Connections between the patient monitoring system 10 and the other devices (not shown) can be made through local area networks ("LANs"), wide area networks ("WANs"), public switched telephone networks ("PSTNs"), intranets, the Internet, and other networks. In a hospital or medical care facility, communication between the patient monitoring system 10 and the other devices (not shown) can be made through the Health Level Seven ("HL7") protocol with any version and/or other required protocol. HL7 is a standard protocol which specifies the implementation of interfaces between two computer applications (sender and receiver) from different vendors for electronic data exchange in health care environments. HL7 allows health care institutions to exchange key sets of data from different application systems. Specifically, HL7 defines the data to be exchanged, the timing of the interchange, and the communication of errors to the application. The formats are generally generic in nature and can be configured to meet the needs of the two applications involved.

In one embodiment of the invention, the data acquisition module 30 of the patient monitoring system 10 can acquire data from the electrodes 22 and data from the implant 18 at the same time. The data can be in the form of, but is not limited to, measurements, waveforms, raw data, processed data, numerical representations, time periods, etc. The implant and non-implant data can include, but is not limited to, one or more of the following: heart rate; blood oxygen saturation; blood pressure; respiration rate; body temperature; ECG data; QRS duration; Q and R wave amplitude and duration; T-wave amplitude, duration, polarity, and alternans; Q-T angle; autonomic turbulence; heart rate variability; wall motion abnormalities; ejection fraction; electrical gradient across the ventricular wall; depolarization time; repolarization time; timing and coupling intervals; cardiac output; pacing protocol; energy consumption; patient activity; etc.

In some embodiments, the data acquisition module 30 can acquire data from the electrodes 22 and data from the implant 18 in real-time. The data acquired from the implant 18 can be transmitted wirelessly from the implant 18 to the patient monitoring system 10 or to the wireless device 42. If the implant data is transmitted to the wireless device 42, the implant data can be transmitted or downloaded from the wireless device 42 to the patient monitoring system 10, either wirelessly or with the appropriate hardware.

Alternatively, if the data is not analyzed and/or reviewed in real-time, the patient monitoring system 10 can assign to the data the date and time when the data was acquired by use of an internal timing system, such as an atomic clock. The implant and non-implant data can be saved and reviewed by caregivers at a later time. When the implant and non-implant data is to be analyzed and reviewed, the implant data can be time-synchronized with the non-implant data by the patient monitoring system 10 based on the date and time when the implant and non-implant data was acquired. In other embodiments, if implant and non-implant data was not acquired during the same date and time, the implant data can be aligned with the non-implant data according to one or more fiducial points (e.g., QRS complexes).

After the implant and non-implant data has been acquired by the data acquisition module 30, the data can be transmitted to the analysis module 34. The analysis module 34 can use a correlation algorithm to correlate the implant data to the non-implant data. The correlation algorithm can be based on a statistical or linear regression model or any other suitable mathematical technique. The results of the correlation algorithm can provide a signature pattern 50, which can be compared with other data and/or other signature patterns previously acquired from the patient 14. The signature pattern 50 can also be stored in the patient monitoring system 10 and/or in any suitable database (not shown) connected to the network 46. The signature pattern 50 can be used to determine whether a cardiac event has occurred in the patient 14 and/or how the implant 18 reacted to or was affected by the cardiac event. The signature pattern 50 can also be used to determine the effectiveness of the current treatment, to determine whether a new diagnosis is warranted, and/or to recommend a new treatment for the patient 14.

In addition, the signature pattern 50 can be used to determine the point at which treatment was applied to the patient 14 and the effect the treatment had on the patient's implant and non-implant data. In other words, the signature pattern 50 can be used to identify when and to reflect the effectiveness of treatment or therapy, such as artificial vagal stimulation, artificial hormonal stimulation, artificial cardiac pacing, artificial airway stimulation, defibrillation, and cardiac resynchronization.

If time-synchronized implant data is not available or cannot be obtained, non-implant data can be acquired and compared to a previously-acquired implant data signature pattern 50. The previously-acquired implant data that was used to generate the implant data signature pattern 50 can generally also be recognized in the non-implant data. For example, artificial stimulation of R waves at specified varying intervals by the implant 18 can be recognized in the non-implant data.

In one example situation, the patient 14 may be in an electrophysiology lab undergoing tests in which arrhythmias and other cardiac conditions are electrically provoked and measured to obtain a signature pattern 50. In this case, the signature pattern 50 can identify the event that was provoked and can reflect the reaction of the implant 18. Both implant and non-implant data can be acquired in real-time while the patient 14 is in the electrophysiology lab and can be reviewed by caregivers on a display of the patient monitoring system 10. The implant and non-implant data acquired can show a different perspective, and thus, a potentially different diagnosis and treatment recommendation than if data from only the implant or data from only the non-implant source was reviewed by the caregivers.

In another example situation, the patient 14 may be undergoing a stress test (pharmaceutical or conventional), which can provoke clinical conditions that can be measured to obtain a signature pattern 50. In yet another example situation, the implant 18 can provoke clinical conditions, such as artificial pacing of the heart at a rapid rate. This event can provide a signature pattern 50 specifically reflecting that the implant 18 was artificially pacing the heart. In still another example situation, the implant 18 can obtain certain measurements, such as autonomic turbulence, via a pacing protocol with shorter or longer coupling intervals. In general, the signature patterns 50 in any of these example situations can be stored and used as future references to which subsequently-acquired data can be compared to determine the functionality of the implant 18 and/or to detect changes in the patient's cardiovascular system.

In general, the criteria for the detection of diseases and the prediction of poor outcomes based only on non-implant data are well established. Based on certain symptoms, caregivers can order specific tests to be performed on the patient 14. The results of those tests, (i.e., the non-implant data only), can be analyzed and reviewed by the caregivers to detect the presence of disease, to detect whether a certain cardiac event occurred, to determine a diagnosis, and to recommend treatment or other tests. However, criteria for the detection of diseases and the prediction of poor outcomes based on only implant data are yet to be established.

Acquiring and correlating implant and non-implant data using the patient monitoring system 10 can provide a basis for establishing criteria for the diagnosis and treatment of disease based on implant data only. For example, if a certain ECG pattern acquired in non-implant data is known to represent S-T elevation and requires treatment X, the ECG pattern acquired from the implant 18 at the same time must also represent S-T elevation and must also require treatment X. In other words, the implant and non-implant data can be correlated to establish that the ECG pattern acquired with the implant 18 also represents S-T elevation and also requires treatment X. The process of comparing known criteria based on non-implant data with unknown criteria based on implant data can help develop criteria for implant data only. According to one embodiment of the invention, the patient's implant 18 can be interrogated and the implant data can be compared to now known criteria in order to determine a diagnosis, recommend treatment, and detect whether the implant 18 is operating properly.

In addition, each patient 14 can develop over time individual known criteria and patterns for certain diseases based on implant data only. Each time the implant 18 is interrogated, the implant data can be compared to the patient's known criteria and patterns to detect whether the disease state has changed, whether the patient's cardiovascular system has changed, or whether the implant 18 has modified its own operation.

In some embodiments, by correlating implant and non-implant data, known criteria and patterns for implant data only can be developed for any one or more of the following: QRS duration (paced or non-paced beats), morphology, and polarity; Q or R-wave amplitude and duration; T-wave amplitude, duration, polarity, and alternans; Q-T angle; wall motion abnormalities; ejection fraction; etc.

Correlating implant and non-implant data can also be used to improve the therapy provided by the implant 18 for subsequent events or for recommending alternative treatment strategies that can be provided by the implant 18. Non-implant data acquired in relation to an onset of implant therapy can be used to better identify a cardiac problem or disease. For example, non-implant data can identify a cardiac problem with timing interval, focus, re-entrant pathway, or bypass track that caused the implant 18 to provide therapy to the patient 14. The caregiver can change one or more settings on the implant 18 or provide other therapy, such as electrophysiology ablation, to treat the cardiac problem. The problem may not have been detected if the caregiver could review only the implant data or only the non-implant data. However, by reviewing the correlation of the implant data and the non-implant data, the caregiver can determine whether the therapy supplied by the implant 18 was effective.

Non-implant data can also be used to trend and identify predictors for therapy that can be provided by the implant 18.

For example, the patient monitoring system 10 can trend and identify predictors including one or more of QRS duration (paced or non-paced beats), heart rate variability, QT prolongation, late potentials, T-wave abnormality, PR interval prolongation, QRS conduction defects, P-wave conduction defects, repolarization abnormalities, etc. By reviewing correlated implant and non-implant data, the caregiver can identify problems that led to the therapy provided by the implant 18. In one embodiment, the patient monitoring system 10 can use correlated implant and non-implant data to provide the placement and settings for a bi-ventricular pacemaker in relation to such values as wall motion, ejection fraction, cardiac output, renal function, etc.

Figure 3:
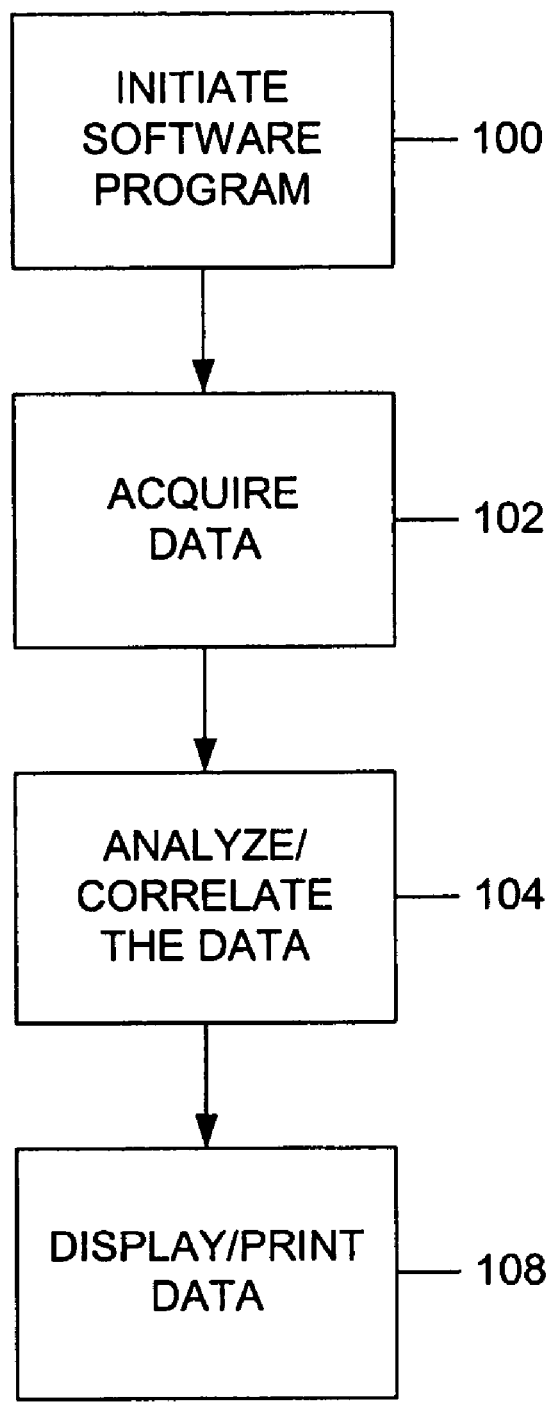
FIG. 3 is a flow chart illustrating the operation of the patient monitoring system according to one embodiment of the invention.

FIG. 3 illustrates one embodiment of the method of the invention. The patient monitoring system 10 can initiate (at 100) the software program 26 to acquire (at 102) data from the patient 14 with the data acquisition module 30. The data acquisition module 30 can acquire non-implant data from the patient 14 via the electrodes 22 and implant data from the patient 14 via the wireless device 42 and/or the receiver 38.

The analysis module 34 can receive the data and can analyze and correlate (at 104) the implant and non-implant data. The correlated data (i.e., the signature patterns 50), the implant data, and/or the non-implant data can be displayed by the patient monitoring system 10 using a computer terminal or any monitor capable of displaying (at 108) data. The computer terminal or display monitor can be remote from the patient monitoring system 10. The correlated, implant, and/or non-implant data can also be printed (at 108) at a printer.

Figure 4:
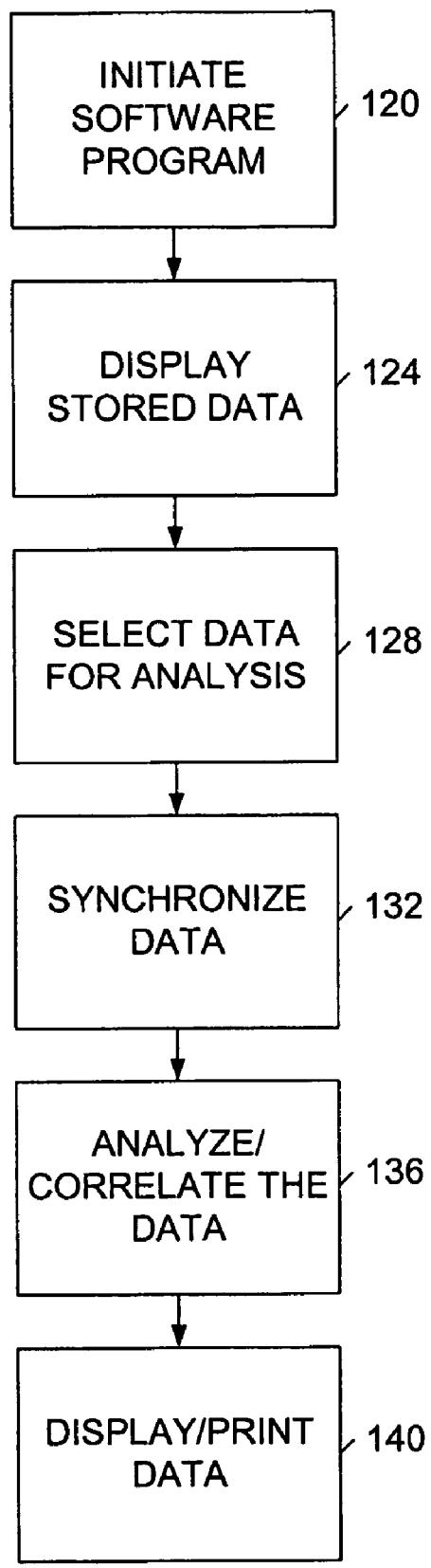
FIG. 4 is a flow chart illustrating the operation of the patient monitoring system according to another embodiment of the invention.

FIG. 4 illustrates another embodiment of the method of the invention. The patient monitoring system 10 can initiate (at 120) the software program 26 to display (at 124) stored data that was previously acquired from the patient 14 with the data acquisition module 30. The data acquisition module 30 can acquire non-implant data from the patient 14 via the electrodes 22 and implant data from the patient 14 via the wireless device 42 and/or the receiver 38. The implant data and the non-implant data can be stored in a database or a server connected directly or via the network 46 to the patient monitoring system 10 or the data acquisition module 30.

If the implant data and non-implant data are not acquired and/or analyzed at the same time, the caregiver can select (at 128) the specific patient data that has been stored in the database or server for review. The software program 26 can synchronize (at 132) the implant data and non-implant data via time-synchronization techniques and/or alignment alignment techniques (e.g., fiducial points). After the implant and non-implant data has been synchronized, the analysis module 30 can receive the data and can analyze and correlate (at 136) the implant and non-implant data. The correlated data (i.e., the signature patterns 50), the implant data, and/or the non-implant data can be displayed (at 140) by the patient monitoring system 10 using a computer terminal or any monitor capable of displaying data. The computer terminal or display monitor can be remote from the patient monitoring system 10. The correlated, implant, and/or non-implant data can also be printed (at 140) at a printer.

Various features and advantages of the invention are set forth in the following claims.

What is claimed is:

1. A patient monitoring system for analyzing cardiac data acquired from a patient having an electronic cardiac implant, the system comprising:
   a transmitter that generates a polling signal;
   a receiver that receives implant data when the implant responds to the polling signal;
   a computer-readable medium encoded with a software program, the software program sets forth rules for:
      a data acquisition module that acquires non-implant cardiac data from the patient, wherein the data acquisition module is not coupled with the receiver, and
      an analysis module that correlates the implant cardiac data and the non-implant cardiac data and generates a signature pattern from the correlation; and
   a processor, the processor configured to execute the software program and carry out the rules for the data acquisition module and the analysis module.

2. The system of claim 1 and further comprising a wireless device operable to interrogate the implant, receive the implant cardiac data, and transmit the implant cardiac data to the receiver.

3. The system of claim 1 and further comprising a network wherein the patient monitoring system is adapted to communicate with additional devices that are connected to the network.

4. The system of claim 3 wherein the data acquisition module acquires via the network implant cardiac data and non-implant cardiac data stored in the additional devices.

5. The system of claim 1 and further comprising displaying at least one of the non-implant cardiac data, the implant cardiac data, and the signature pattern on a display monitor remote from the patient monitoring system.

\* \* \* \* \*